United States Patent [19]
Betts et al.

[11] Patent Number: 5,344,535
[45] Date of Patent: Sep. 6, 1994

[54] DIELECTROPHORETIC CHARACTERIZATION OF MICRO-ORGANISMS AND OTHER PARTICLES

[75] Inventors: Walter B. Betts, Wilberfoss; Jeremy J. Hawkes, Fishergate, both of England

[73] Assignee: British Technology Group Limited, London, England

[21] Appl. No.: 53,326

[22] Filed: Apr. 27, 1993

Related U.S. Application Data

[63] Continuation of Ser. No. 730,888, Jul. 22, 1991, abandoned.

[30] Foreign Application Priority Data

Nov. 27, 1989 [GB] United Kingdom ............ 8926781.9

[51] Int. Cl.$^5$ .................... G01N 27/26; G01N 27/447
[52] U.S. Cl. ................... 204/183.1; 204/180.1; 204/299 R
[58] Field of Search ............ 204/299 R, 180.1, 183.1, 204/183.3

[56] References Cited

U.S. PATENT DOCUMENTS

| | | | |
|---|---|---|---|
| 4,326,934 | 4/1982 | Pohl | 204/183.1 |
| 4,476,004 | 10/1984 | Pohl | 204/299 R |
| 4,578,167 | 3/1986 | Schoner | 204/183.1 |

OTHER PUBLICATIONS

Julian P. H. Burt et al. "An optical dielectrophoresis spectrometer for low-frequency measurements on colloidal suspensions" J. Phys. E: Sci. Instrum 22 (1989) 952–957.

Richard J. Adamson and Karan V. I. S. Kaler "An Automated Stream-Centered Dielectrophoretic System" IEEE Transactions on Industrial Applications, vol. 24, No. 1 (Jan./Feb. 1988) 93–98.

Price et al. "An Optical Technique for Measurement of Cell Dielectrophoresis", 1987, pp. 75–79.

Fujii H., "Measuring Apparatus for Electrophoresis of Suspended Particle", Patent Abstracts of Japan, 1982, vol. 6, No. 62.

*Primary Examiner*—John Niebling
*Assistant Examiner*—John S. Starsiak, Jr.
*Attorney, Agent, or Firm*—Nixon & Vanderhye

[57] ABSTRACT

Dielectrophoretic collection rates of micro-organisms or other animate or inanimate dielectrically polarizable particles in suspension in a fluid are established by flowing the suspension past electrodes energized to produce a non-uniform alternating electric field in the suspension, terminating the energization of the electrodes after a predetermined time to release particles collected from the suspension, and, downstream of the electrodes, measuring the pulse of released particles as a measure of the rate of particle collection during energization of the electrodes. Repeated measurements at different field frequencies enable a collection-rate spectrum to be established and the particles under examination to be characterized or identified by reference to known spectra of known particles.

6 Claims, 3 Drawing Sheets

DIELECTROPHORETIC CHARACTERIZATION OF MICRO-ORGANISMS AND OTHER PARTICLES

This is a continuation of application Ser. No. 07/730,888, filed Jul. 22, 1991, now abandoned.

The invention relates to a method and apparatus for the characterisation or identification of micro-organisms and other particles, utilising the phenomenon of dielectrophoresis.

It is well known that dielectrically polarisable particles suspended in a medium in a non-uniform electrical field are subject, even if they bear no net charge, to a "dielectrophoretic" force tending to move them (according as their polarisability is greater or less than that of the medium) in the direction of increasing or decreasing strength of the electric field, the force F to which a particle of volume v and effective polarisability p is subject being given by the relation $$F = pv (E \cdot \nabla) E$$

where E is the electric field strength at the position of the particle and $\nabla$ is the del vector operator. In an alternating field in which the field strength at any point is oscillatory but in which the field pattern remains stationary, the dielectrophoretic force on a particle is unidirectional, though its magnitude varies cyclically, and the resulting motion of the particle is also unidirectional, such as to move it, if its polarisabitity is greater than that of the surrounding medium, towards increasing strength of field and, usually, towards one or another of a system of electrodes between which the field is produced. The use of an alternating field has the advantage that It imposes on a particle no net force due to any net electrical charge on the particle, since any such force is itself alternating and its average over a cycle is zero.

It has been proposed to use the dielectrophoretic effect for collecting biological cells from an aqueous or other fluid suspension containing such cells, by placing the suspension in a container provided with a system of electrodes so that the electrodes are immersed in the suspension, and then applying a voltage (usually alternating) between the electrodes so that cells in the suspension (moving always in the direction of increasing field strength at their own immediate location) are caused to move towards one or other of the electrodes and to collect on the electrodes or in their immediate vicinity. As described in a paper by J. A. R. Price, J. P. H. Burr and R. Pethig in Biochimica et Biophysica Acta 964 (1988), pages 221–230, the rate of collection of the cells has been observed and measured photometrically by shining a light through the Inter-electrode gaps and measuring the intensity of the beam of light after transmission; the reduction in transmitted light intensity, due to increased absorption or scattering of the light as cell collection proceeds, gives a measure both of the total of cells collected and of the rate of cell collection as a function of time. Usually the rate of collection is greatest initially and then falls off, due both to reducing concentration of cells remaining In the suspension and to a screening or saturation effect due to the presence at the electrodes of the cells already collected.

As reported in the above-mentioned paper, it has been found that the rate of collection of cells is also a function of the frequency of the applied electric field, i.e. of the voltage applied to the electrodes. For any one type of cell (or other particle) a collection-rate spectrum, i.e. a curve relating cell collection rate to frequency of the applied electric field, can be established over a field-frequency range from, say, 100 Hz to 10 MHz; and it is found that cells of different kinds have significantly different collection-rate spectra.

It might be hoped that this fact, that cells of different kinds possess different collection-rate spectra, might enable the unknown suspended constituents of a fluid suspension of micro-organisms to be identified by establishing a composite or aggregate collection-rate spectrum for the suspension as a whole and then analysing that spectrum in terms of the known spectra of individual possible constituents and the proportions in which such individual spectra could be combined additively to yield a composite spectrum corresponding to that established experimentally.

However, with the known apparatus by means of which such a composite spectrum could be established, the time and effort required for doing so would be inconveniently great since after every determination of the collection rate at one frequency the container containing the sample of suspension being investigated would have to be flushed and filled with a fresh sample or, at least, the existing sample would have to be restored to its original pre-investigation condition, by vigorous agitation for example, in a manner which cannot easily be envisaged since it is essentially stagnant. Furthermore, monitoring the collection rate by means of a light beam which shines only through inter-electrode gaps is an unsatisfactory expedient since it gives no direct information about collected particles which are concealed "behind" the electrodes.

It is an object of the present invention to provide improved apparatus for establishing dielectrophoretic collection rates and collection-rate spectra for dielectrically polarisable particles in a suspension and an improved method, using such apparatus, of establishing such collection rates and collection-rate spectra and of thereby characterising or identifying such particles in suspension by reference to known collection-rate spectra of known types of particle. Particles to which the invention may be applied include various kinds of animate particles such as micro-organisms and cells such as blood cells, sub-cellular particles such as viruses and plasmids, and inanimate-material particles such as latex beads, which may or may not be coated with animate materials; and in the following disclosure references simply to particles, for the sake of brevity, are intended to be understood in this broad way.

According to one aspect of the invention, there is provided apparatus for establishing dielectrophoretic collection rates for particles in a fluid suspension, comprising a chamber for the suspension fluid, an electrode system disposed to influence such fluid within the chamber, means for applying an alternating voltage between electrodes of the electrode structure and thereby establishing in such fluid a spatially non-uniform alternating electric field thereby to induce dielectrophoretic collection adjacent such electrodes of electrically polarisable particles suspended in the fluid, and means for measuring particle concentration at a location within the chamber, wherein the chamber is provided with an inlet and an outlet, so disposed that fluid flowing through the chamber from the inlet to the outlet flows past the electrode structure and then through the said location, and with means arranged to produce such fluid flow through the chamber.

The means arranged to produce fluid flow through the chamber may be fluid circulating means arranged to re-circulate fluid from the outlet to the inlet of the chamber.

The means for measuring micro-organism or other particle concentration is preferably of the kind already described, comprising a light source arranged to project a beam of light through the chamber (but at a location downstream of, instead of at, the electrode structure) and light detector means sensitive to the intensity of the light beam after transmission through the chamber and thus to the increased or decreased absorption or scattering of the light beam which indicates an increase or decrease in the concentration of micro-organisms or other particles suspended in the fluid traversed by the light beam.

According to a further aspect of the invention there is provided a method of establishing dielectrophoretic collection rates for dielectrically polarisable particles in a fluid suspension, comprising: causing the suspension fluid to flow past an electrode structure, energising the electrode structure for a predetermined time interval with an alternating voltage at a preselected frequency and thereby establishing in the flowing fluid a spatially non-uniform alternating electrical field and inducing dielectrophoretic collection, adjacent the electrode structure, of dielectrically polarisable particles suspended in the fluid, thereafter terminating the energisation of the electrode structure and thereby releasing the particles collected adjacent thereto, and measuring the pulse of increased particle concentration at a location downstream of the electrode structure which occurs as the released particles are carried through such location by the flowing fluid.

Preferably this method according to the invention is carried out using the above-Indicated apparatus according to the invention.

It will be appreciated that the pulse of increased particle concentration which is carried through the measuring location, following release of collected particles from the electrode structure, is thereafter rapidly dispersed into the suspension fluid during its flow; and the method may be carried out repeatedly, even on a sample which is small and therefore has to be re-circulated, using different frequencies of the applied alternating voltage during successive electrode-structure energisation intervals, in order to produce the data required for establishing either the whole or critical ranges of the collection-rate spectrum of the suspension under examination. The data thus acquired can then be correlated with corresponding known data relating to the collection-rate spectra of particular micro-organisms or other particles to establish the relative and/or absolute concentrations of such particles required in the suspension under examination in order that it should yield the collection-rate data which have been acquired.

The invention will be more fully understood from the following more detailed description with reference to the accompanying drawings, in which.

Figure 1:
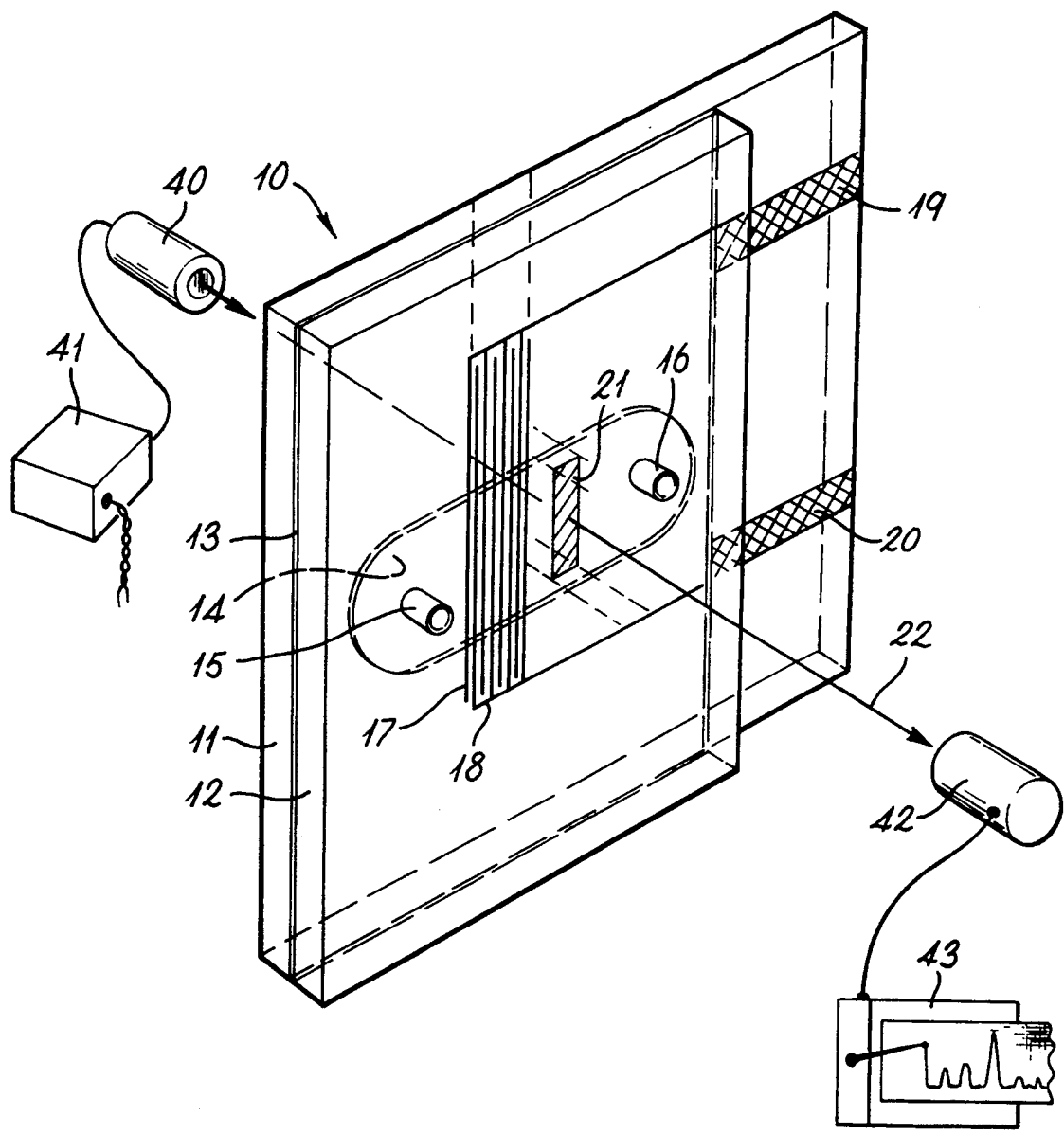
FIG. 1 is a diagrammatic perspective view of a chamber assembly provided with an electrode system for use In accordance with the invention.

The chamber assembly shown in FIG. 1 and indicated generally by the reference 10 comprises a back plate 11 and a front plate 12, both made of glass, and transparent, with a spacer sheet 13 sandwiched between them. A central part of the spacer 13 is removed so as to form a thin chamber 14 (the thickness of the spacer 13 which may be about 0.05 mm but may be within a wide range, depending on the sizes of suspended particles which may be encountered) between the plates 11 and 12, and the plate 12 is provided with an inlet 15 and an outlet 16 open to the chamber 14. The chamber 14 may be some 10 mm in height and 40 mm in length. The back plate 11 has upon it an electrode structure in the form of a metallic layer, for example of aluminium, deposited upon it to a thickness of, say, 1 micron and then etched to provide a pair of interdigitated electrodes 17 and 18 integral with connection terminal tabs 19 and 20 respectively. Each electrode may be formed with eight parallel fingers each 0.06 mm in width and separated by 0.06 mm from each adjacent finger of the other electrode, and the central part of the length of each finger is exposed to the interior of the chamber 14 to be in close proximity to a fluid disposed therein, though a protective film of insulating material may be provided to prevent actual contact between the fluid and the electrodes. The shape of the electrodes is such as to provide a spatially very non-uniform electrical field in their immediate vicinity when a voltage is applied between them. The electrodes 17 and 18 are nearer to the inlet 15 than to the outlet 16, leaving between the electrodes and the outlet 16 a region 21 of the chamber 14 through which a beam of light (for example of 450 or 660 nm wavelength, or another wavelength more suitable for a particular material) indicated by an arrow 22 may be arranged to shine without being obstructed by the electrodes 17 and 18.

Figure 2:
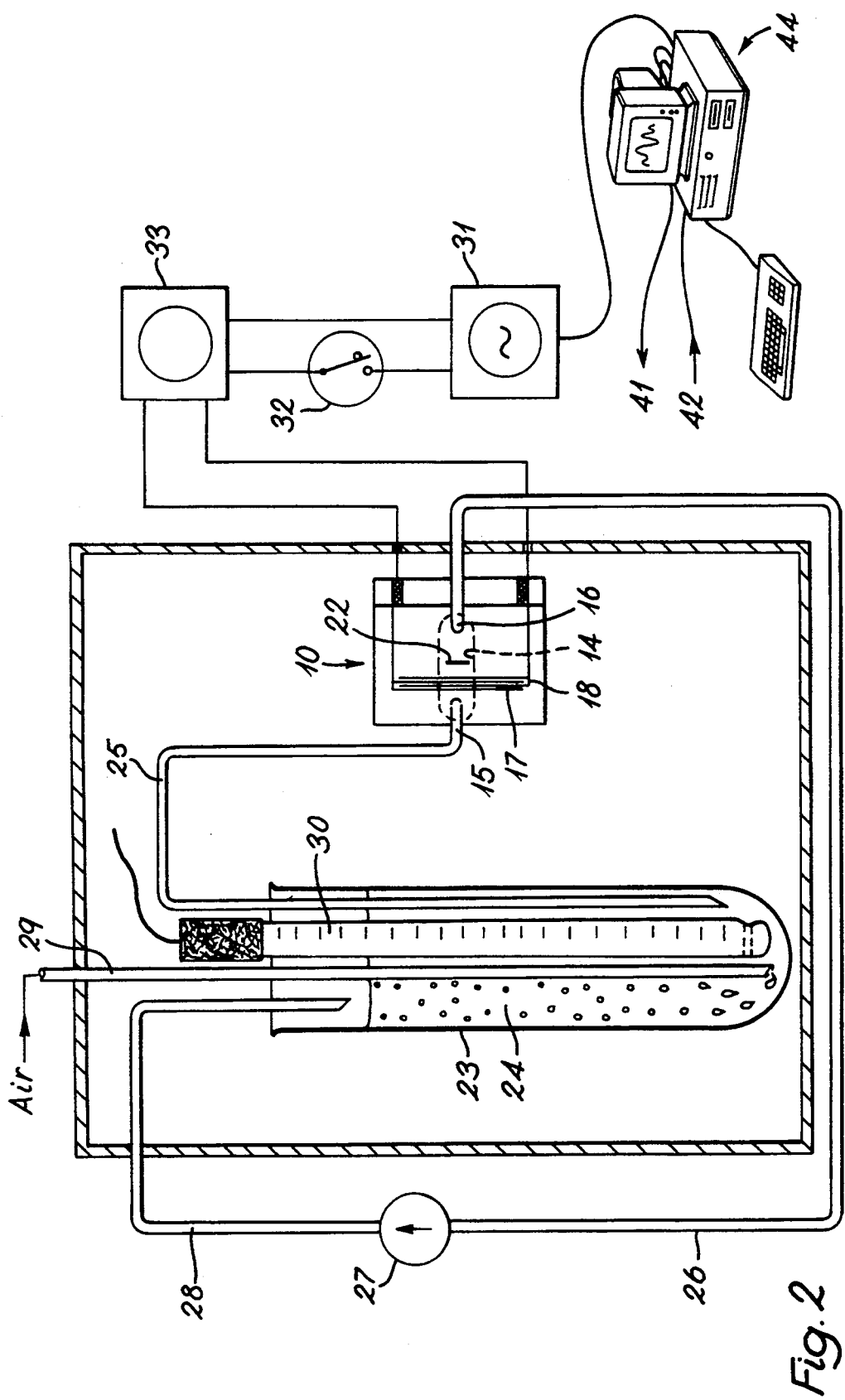
FIG. 2 is a diagrammatic representation of apparatus according to the invention, incorporating the chamber assembly shown in FIG. 1.

The chamber assembly 10 shown in FIG. 1 is incorporated in apparatus according to the invention shown in FIG. 2. This comprises a reservoir 23 of a liquid suspension 24 containing particles, say micro-organisms, which are to be identified. A tube 25 connected to the inlet 15 of the chamber assembly 10 dips into the liquid suspension 24 in the reservoir 23, and the outlet 16 of the chamber assembly is connected by a tube 26 to a pump 27, which may be a peristaltic pump, which draws suspension fluid through the chamber 14 and returns It to the reservoir 23 via a return tube 28, for example at a rate between 0.1 and 1.0 ml per minute. Air from an airline 29 bubbles through the suspension 24 in the reservoir and serves both to agitate the suspension and to keep it aerated. Also extending into the reservoir 23 is a pH probe 30 for monitoring the pH of the suspension 24 to enable it to be maintained at a desired constant level, since it is found that the collection rate of micro-organisms by dielectrophoresis at the electrodes 17 and 18 is dependent on the pH of the suspension. Preferably the whole apparatus is maintained at a desired constant temperature, since temperature variation also tends to affect collection rates.

The apparatus also comprises a signal generator 31 producing an alternating voltage at selected frequency and amplitude which may be applied, by means of a switch 32, to an oscilloscope 33, which serves to monitor it, and to the electrodes 17 and 18 of the chamber assembly 10. Conveniently, the voltage applied to the electrodes has an amplitude selected in the range between 5 and 30 volts, and frequencies which range from 10 Hz to 10 MHz or more. Also provided are a light source, preferably an LED light source 40 energised by a power supply 41 as shown in FIG. 1, arranged to project the light beam 22 through the chamber 14, and a photometer shown as 42 in FIG. 1 which measures the intensity of the beam 22 after it has passed through the chamber 14 and provides an input for a chart recorder 43.

In use of the apparatus, with the pump 27 continuously drawing a flow of the suspension 24 through the chamber 14 and re-circulating it to the reservoir 23, the switch 32 is closed for a period of, say, 5 seconds to apply the voltage from the signal generator 31, at a predetermined amplitude and selected frequency, to the electrodes 17 and 18 and produce a spatially non-uniform alternating electric field in the suspension adjacent the electrodes, resulting in micro-organisms in the suspension being moved dielectrophoretically and collected on or adjacent the electrodes. When the switch 32 is opened, the collected micro-organisms are released and carried downstream by the continuing flow of the suspension liquid, to pass through the light beam 22 as a localised pulse of increased concentration of micro-organisms in the suspension.

Figure 3:
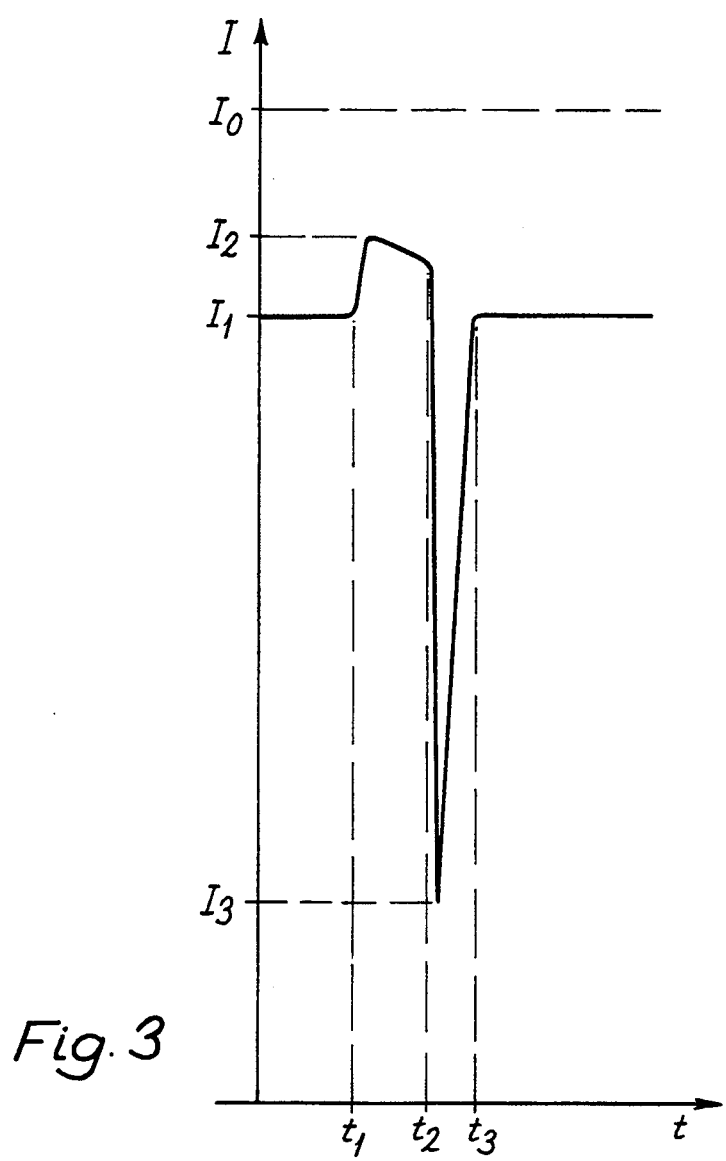
FIG. 3 is a representation of the manner in which absorption of a light beam provided in the apparatus of FIG. 2 varies with time during and after a micro-organism or other particle collection period while the apparatus is in use.

The resulting form of an output signal from the photometer, recorded by the chart recorder 43 and representing the measured intensity I of the light beam 22 as a function of time t, is indicated in FIG. 3. In the absence of an applied voltage on the electrodes 17 and 18 a steady measured beam intensity $I_1$ is less than the value $I_0$ which would represent the beam intensity before it passes through the chamber assembly 10. The difference $I_0-I_1$ represents the intensity loss during passage through the chamber assembly 10, due largely to absorption and/or scattering of light by micro-organisms suspended in the liquid flowing through the chamber 14. When an alternating voltage is applied to the electrodes 17 and 18 at time $t_1$, the measured light intensity rises sharply to a value $I_2$ as micro-organisms begin to be collected on or adjacent the electrodes and their concentration in the fluid downstream, as it passes through the light beam 22, is rapidly reduced. In the interval until time $t_2$ when the applied voltage is switched off, the collection rate at the electrodes begins to fall off and the measured intensity of the light beam begins to fall as the micro-organism concentration downstream of the electrodes begins to rise correspondingly. Removal of the applied voltage at time $t_2$ results in a sudden release from the electrodes of the collected micro-organisms which are carried downstream as a highly localised pulse of increased micro-organism concentration in the flowing suspension, resulting in a sharp reduction in the beam intensity to a low value $I_3$ as the pulse passes through the beam. At a slightly later time $t_3$, the pulse has passed and the measured beam intensity has returned to its steady value $I_1$. The increase in absorption represented by the intensity difference $I_1-I_3$ is (by a factor of perhaps 100) a much more sensitive measure of the quantity of micro-organism(s) collected in the interval from $t_1$ to $t_2$, and thus of the initial collection rate, than is the relatively small rise in intensity from $I_1$ to $I_2$ which is the direct consequence of the collection rate.

Once the pulse of increased-concentration suspension has passed through the light beam 22, it is rapidly dispersed as it is pumped back into the reservoir 23 and is there further agitated by air from the air line 24. Successive applications of alternating voltage to the electrodes 17 and 18 at different frequencies, preferably automatically, under the control of a computer 44 as shown schematically in FIG. 2, can follow one another in quick succession to establish the data which, stored by the computer, will define the collection-rate spectrum of the fluid under examination. Thus the time required to obtain a collection spectrum over a frequency range from 10 Hz to 1 MHz may be reduced from more than a day, by methods known hitherto, to 5 minutes or less. Comparison of the defining data of the spectrum thus obtained with corresponding data from known spectra of selected individual micro-organisms or other possibly relevant particles, to obtain an analysis of the particle content of the sample under examination, can also be rapidly effected using a suitable computer program, so that analyses of samples can be rapidly performed using the apparatus and method of the invention.

Figure 4:
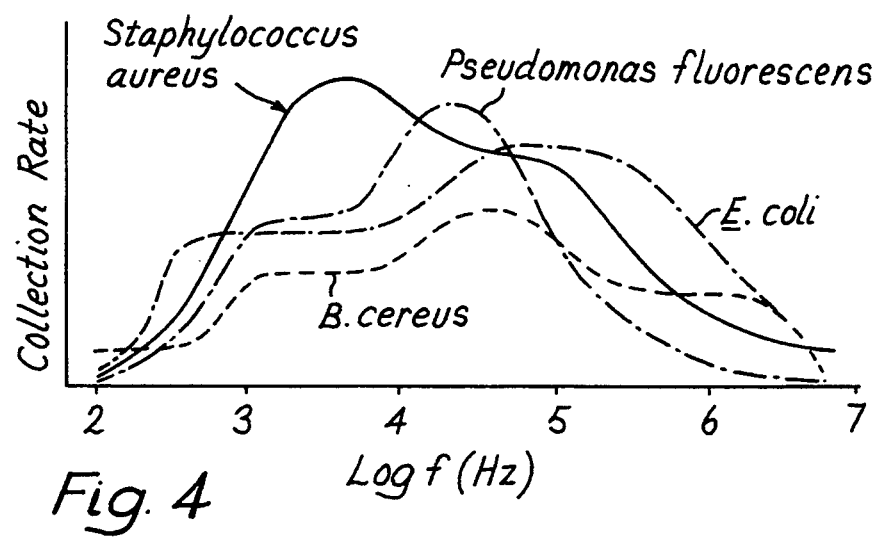
FIG. 4 is a representation of collection-rate spectra of four different micro-organisms, as established by previous workers and available in the published prior art.

Collection-rate spectra for four micro-organisms as known from previous work are shown in FIG. 4, in which the curves 34, 35, 36 and 37 respectively represent the collection-rate spectra of *Staphylococcus aureus, Pseudomonas fluorescens, E. coli* and *B. cereus.* Rather than adopt such previous results uncritically as reference spectra, it may be preferable for use with a particular apparatus according to the invention to build up a library of such reference spectra as obtained using that apparatus with the operating conditions established as they will be set during subsequent use of the apparatus. In general, however, the apparatus requires only a very low level of routine calibration, while nevertheless providing a markedly increased sensitivity, greater selectivity for microbial and other particle types and much improved speed and simplicity of operation as compared with previously available apparatus.

As mentioned above, the electrodes 17 and 18 may be of aluminium, and formed by depositing a layer of the metal on the glass plate 11 and then etching to provide the required electrode pattern. Instead of aluminium, platinum or gold-plated chromium electrodes may be employed, produced either by an etching technique or by a "lift-off" technique in which a pattern mask is formed on the substrate, using a suitable material such as a photoresist material, before a metal layer is deposited and unwanted regions of deposited metal are then removed by removing the pattern mask so as to leave the metal only where it was deposited directly on the substrate.

We claim:

1. Apparatus for establishing dielectrophoretic collection rates for particles in a fluid suspension, said apparatus comprising:
   a chamber for said fluid suspension, said chamber having an inlet and an outlet;
   an electrode system comprising closely spaced interdigitated electrodes for influencing said fluid suspension within said chamber;
   means for applying an alternating voltage between said interdigitated electrodes of said electrode system and thereby establishing in said fluid suspension in the immediate vicinity of said electrodes a spatially non-uniform alternating electric field thereby to induce dielectrophoretic collection adjacent said electrodes of electrically polarizable particles suspended in said fluid suspension;

means for producing fluid flow of said fluid suspension through said chamber; and means for measuring particle concentration at a measuring region within said chamber, said inlet and outlet being so disposed that fluid suspension flowing through said chamber from said inlet to said outlet flows past said electrode system and immediately thereafter past said measuring region within said chamber.

2. Apparatus as claimed in claim 1, wherein said means for producing fluid flow in fluid circulating means for re-circulating fluid from said outlet to said inlet of said chamber.

3. Apparatus as claimed in claim 1, wherein said means for measuring particle concentration comprises a light source arranged to project a beam of light through said chamber at said measuring region, immediately downstream of said electrode system, and light detector means sensitive to the intensity of said light beam after transmission through said chamber and thus to increased or decreased absorption or scattering of said light beam which indicates an increase or decrease in concentration of particles suspended by said fluid suspension traversed by said light beam at said measuring region.

4. A method of establishing dielectrophoretic collection rates for dielectrically polarizable particles in a fluid suspension, said method comprising the steps of:

causing a fluid suspension to flow in a chamber past an electrode structure;

energizing said electrode structure for a predetermined time interval with an alternating voltage at a preselected frequency and thereby establishing in said flowing fluid suspension a spatially non-uniform alternating electrical field and inducing dielectrophoretic collection, adjacent said electrode structure, of dielectrically polarizable particles suspended in said fluid suspension;

thereafter terminating the energizing of said electrode structure and thereby releasing particles collected adjacent thereto as a localized pulse of increased particle concentration in the flowing fluid suspension; and measuring said pulse of increased particle concentration at a measuring region located within said chamber and immediately downstream of said electrode structure.

5. A method of establishing a dielectrophoretic collection-rate spectrum for particles in a fluid suspension, said method comprising carrying out the method of claim 4 repeatedly, using different frequencies for the applied alternating voltage during successive electrode structure energization intervals to produce data required for establishing either entire or critical ranges of the collection-rate spectrum of the fluid suspension.

6. A method of identifying dielectrically polarizable particles contained in a fluid suspension, said method comprising establishing a dielectrophoretic collection-rate spectrum data therefor according to the method as claimed in claim 5 and correlating said data thus acquired with corresponding known data relating to the collection-rate spectra of particular identified particles, to establish relative or absolute concentrations of such identified particles required to be present in the suspension under examination in order that it should yield the collection-rate data which have been acquired.

* * * * *